US00PP22212P2

(12) United States Plant Patent
Skotak

(10) Patent No.: US PP22,212 P2
(45) Date of Patent: Oct. 25, 2011

(54) ***GUZMANIA* PLANT NAMED 'DURAMAR'**

(50) Latin Name: *Guzmania wittmackii×lingulata*
Varietal Denomination: Duramar

(76) Inventor: Chester Skotak, Alajuela (CR)

( * ) Notice: Subject to any disclaimer, the term of this patent is extended or adjusted under 35 U.S.C. 154(b) by 0 days.

(21) Appl. No.: 12/799,754

(22) Filed: Apr. 30, 2010

(51) Int. Cl.
*A01H 5/00* (2006.01)

(52) U.S. Cl. ..... Plt./371

(58) Field of Classification Search ..... Plt./371
See application file for complete search history.

*Primary Examiner* — Susan McCormick Ewoldt

(57) ABSTRACT

A new and distinct *Guzmania* hybrid cultivar named 'DURAMAR' is disclosed, characterized by unique bract coloration, shiny bracts and a broad overall inflorescence. The new variety is a *Guzmania,* and is normally used as an ornamental plant.

1 Drawing Sheet

Figure 1:
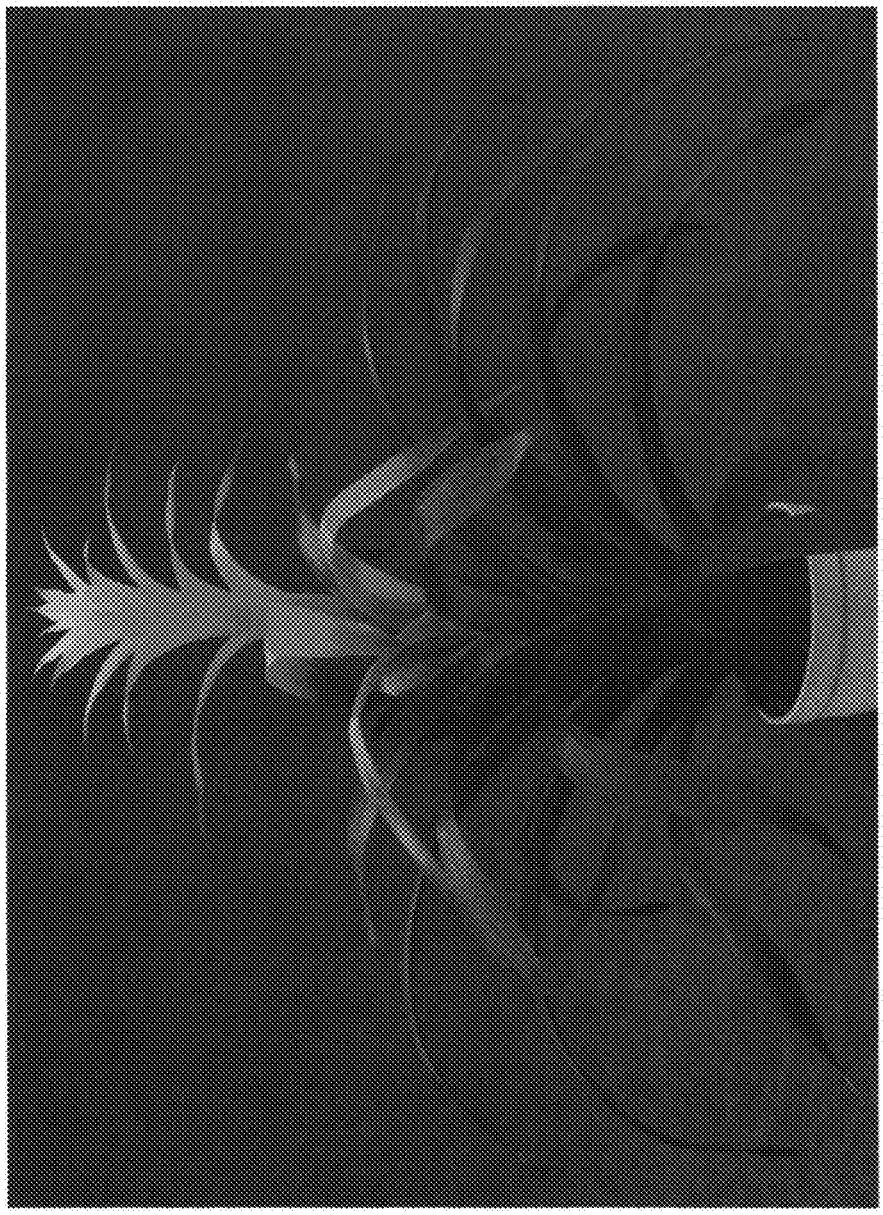

Latin name of the genus and species: *Guzmania wittmackii×lingulata.*

Variety denomination: 'DURAMAR'.

BACKGROUND OF THE INVENTION

The new cultivar is a product of a planned breeding program. The new variety originated from a cross pollination of an unnamed, unpatented, proprietary seedling *Guzmania wittmackii* with an unnamed, unpatented, proprietary seedling *Guzmania lingulata.* The new variety was discovered by the inventor, Chester Skotak Jr., a citizen of Costa Rica, in Ajauela, Costa Rica during 2004, in a group of seedlings resulting from the crossing.

Asexual reproduction of the new cultivar 'Duramar' was first performed in Belgium by tissue culture, in March 2005. 'Duramar' has since produced several generations by tissue culture and has shown that the unique features of this cultivar are stable and reproduced true to type.

SUMMARY OF THE INVENTION

The cultivar 'DURAMAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DURAMAR.' These characteristics in combination distinguish 'DURAMAR' as a new and distinct *Guzmania* hybrid cultivar:

1. Unique bract coloration.
2. Shiny bracts.
3. Broad overall inflorescence.

PARENT COMPARISON

Plants of the new cultivar 'DURAMAR' are similar to plants of the seed parent variety, an unnamed, unpatented, proprietary seedling of *Guzmania wittmackii,* in most horticultural characteristics. However, plants of the new cultivar 'DURAMAR' produce purple-tipped bracts, whereas the seed parent produces bracts only colored yellow and orange. Additionally, the new variety has a wider flower than the seed parent, and shinier bracts than the seed parent.

Plants of the new cultivar 'DURAMAR' are similar to plants of the pollen parent variety, an unnamed, unpatented, proprietary seedling of *Guzmania lingulata,* in most horticultural characteristics. However, plants of the new cultivar 'DURAMAR' are taller and do not have a white upper bract coloration found on the pollen parent.

COMMERCIAL COMPARISON

Plants of the new cultivar 'DURAMAR' are similar to plants of the unpatented commercial variety, *Guzmania* hybrid 'Marjan' in most horticultural characteristics. However, plants of the new cultivar 'DURAMAR' produce purple tipped bracts, not found on 'Marjan' and 'DURAMAR' produces shinier bracts than 'Marjan.'

BRIEF DESCRIPTION OF THE PHOTOGRAPH

The accompanying photograph in FIG. 1 illustrates in full color a typical plant of 'DURAMAR' grown in a greenhouse. The pot size is a commercial 11 cm container. The plant shown is approximately 18 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DURAMAR' plants grown in a commercial controlled greenhouse in Evergem, the Netherlands. Temperatures ranged from 20° C. to 28° C. night and day. No artificial light, photoperiodic treatments or chemical treatments were given to the plants. Measurements and numerical values represent averages of typical plant types.

Botanical classification: *Guzmania wittmackii×lingulata* 'DURAMAR'.

Age of plant described: Approximately 18 months.

Container size of plant described: Approximately 18 cm.

PROPAGATION

Time to initiate roots: About 70 days at approximately 20-28° C.

Time to produce a rooted cutting/liner: About 125 days at approximately 20-28° C.

Root description: Moderately dense, moderately branched, fine, fibrous, not fleshy, colored near RHS Grey 201C.

PLANT

Growth habit: Upright, monopodial.

Height: Average: 42.6 cm.

Plant spread: Average: 58.4 cm.

Normal pot size: 18 cm.

Growth rate: Moderate.

Branching characteristics: Monopodial, leaves form a basal rosette, inflorescence grows from the center of the rosette.

Number of leaves per scape: Average: 14.

Stem length: No stems present, scape grows directly from rosette.

FOLIAGE

Leaf:

*Arrangement.*—Rosulate; leaves (average: 14) placed in a basal rosette.

*Average length.*—Approximately 34.2 cm.

*Average width.*—Approximately 3.5 cm.

*Shape of blade.*—Ligulate.

*Aspect.*—Arching downward.

*Apex.*—Apiculate.

*Base.*—Sheathing. Sheath length: Average 5.0 cm. Sheath width: Average 5.7 cm. Sheath color: Ranging from near RHS Yellow-Green 152D to Greyed Yellow 161B.

*Margin.*—Entire.

*Texture of top surface.*—Smooth, very glossy.

*Texture of bottom surface.*—Smooth, very glossy.

*Color.*—Young foliage upper side: Near RHS Green 143A. Young foliage under side: Near RHS Yellow-Green 146A. Mature foliage upper side: Near RHS Green N137B. Mature foliage under side: Near RHS Yellow-Green 146A.

*Venation.*—Type: Parallel. Venation coloration: Near RHS Green N137B.

Petiole: No petioles present, leaves sheathing.

INFLORESCENCE

General description:

*Inflorescence height, excluding scape.*—Approximately 21.8 cm.

*Inflorescence width.*—Approximately 22.5 cm.

Scape:

*Length.*—Approximately 24.0 cm.

*Width.*—Approximately 1.2 cm.

*Aspect.*—Approximately 90° angle to rosette (near vertical).

*Strength.*—Very strong.

*Color.*—Near RHS Yellow-Green N144D.

Bracts:

*Scape/lowermost bracts.*—Shape: Ligulate. Length: Approximately 28.7 cm, excluding sheath. Width: Approximately 3.8 cm. Quantity: Average 6. Tip: Apiculate. Base: Sheathing. Sheath length: Approximately 4.1 cm. Sheath width: Approximately 2.3 cm. Sheath color: Near RHS Yellow-Green 146C. Margin: Color Upperside: Upper ⅓ of the leaf blade between RHS Green N137B to Yellow-Green 146A, closest to N137B, lower ⅔ of the leaf blade near RHS Red 42A. Tip near Greyed-Purple N187. Color Underside: Upper ⅓ of the leaf blade in between near RHS Yellow-Green 147B and Yellow-Green 148A, lower ⅔ of the leaf blade near RHS Red 45A. Edge of the lower ⅔ and upper ⅓ the leaf blade is colored near RHS Greyed-Purple 185B. Tip near Greyed-Purple N187.

*Terminal bracts.*—Shape: Short ligulate to narrow triangular. Length: Approximately 9.7 cm, excluding sheath. Width: Approximately 3.4 cm. Quantity: Average 14. Tip: Acute. Base: Sheathing. Sheath length: Approximately 2.1 cm. Sheath width: Approximately 2.5 cm. Sheath color: Near RHS Yellow-Green 151B. Margin: Entire. Coloration Terminal Bracts: Upperside: Near RHS Orange-Red 30C, base near RHS Orange-Red 34A. Streaks throughout near Yellow-Orange 16A. Tip near Red-Purple 59B. Underside: Near RHS Orange-Red N30A. Tip near Red-Purple 59B.

OTHER CHARACTERISTICS

Disease resistance: Neither resistance nor susceptibility to diseases or pests has been observed in this variety.

Drought tolerance and cold tolerance: Observed to tolerate temperatures to 40° C. without any negative effects. Temperature tolerance above this range has not been observed. Tolerance of cold temperatures has not been observed.

Fruit/seed production: Not observed.

What is claimed is:

1. A new and distinct cultivar of *Guzmania* plant named 'DURAMAR' as herein illustrated and described.

* * * * *